United States Patent [19]

Smith et al.

[11] Patent Number: 5,422,248
[45] Date of Patent: Jun. 6, 1995

[54] DNA SEQUENCES ENCODING GRANULOCYTE-COLONY STIMULATING FACTOR RECEPTORS

[75] Inventors: Craig A. Smith; Alf D. Larsen; John E. Sims; Benson M. Curtis, all of Seattle, Wash.

[73] Assignee: Immunex Corporation, Seattle, Wash.

[21] Appl. No.: 6,183

[22] Filed: Jan. 15, 1993

Related U.S. Application Data

[63] Continuation of Ser. No. 587,329, Sep. 24, 1990, abandoned, which is a continuation-in-part of Ser. No. 522,952, Apr. 3, 1990, abandoned, which is a continuation-in-part of Ser. No. 416,306, Oct. 3, 1989, abandoned, which is a continuation-in-part of Ser. No. 412,816, Sep. 26, 1989, abandoned.

[51] Int. Cl.$^6$ ................. C12N 15/00; C12N 15/11; C12N 15/12

[52] U.S. Cl. ................. 435/69.1; 435/71.1; 435/240.1; 435/240.2; 435/320.1; 536/23.1; 536/23.5

[58] Field of Search ............ 435/69.1, 69.5, 71.1, 435/172.3, 240.2, 240.1, 243, 320.1, 6; 536/23.1, 23.5; 935/22, 27

[56] References Cited

U.S. PATENT DOCUMENTS

4,675,285  6/1987  Clark et al. .

OTHER PUBLICATIONS

Fukunaga et al PNAS vol. 87, 1990, pp. 8702-8706.
Hasegawa et al, Chem Abst vol. 114, 1991, #2456822.
Fukunaga et al, Cell., vol. 61, 1990, pp. 341-350.
Fukunaga et al, JBC 265, 1990, pp. 14008-14015.
Park et al, Blood 74, 1989 pp. 56-65.
Sims et al, Science 1988, vol. 241, pp. 585-589.
Yamasaki et al, Science 1988, vol. 241, pp. 825-828.
Budel et al, Blood 74, 1989, pp. 2668-2673.
Yuo et al, Blood 74, 1989, pp. 2144-2149.
Nicola N A, and D. Metcalf, "Binding of $^{125}$I-Labeled Granulocyte Colony-Stimulating Factor to Normal Murine Hemopoietic Cells," J. Cell. Physiol. 124:313, 1985.
Nicola N A and Metcalf D, "Binding of the differentiation-inducer, granulocyte-colony-stimulating factor, to responsive but not unresponsive cell lines," Proc. Natl. Acad. Sci. USA 81:3765, 1984.
Nicola N A, Begley C G, and Metcalf D, "Identification of the human analogue of a regulator that induces differentiation in murine leukemic cells,"0 Nature 314:625, 1985.
Nicola et al., "Identification of Distinct Receptors for Two Hemopoietic Growth Factors (Granulocyte Colony-stimulating Factor and Multipotential Colony-Stimulating Factor) by Chemical Cross-linking," J. Biol. Chem. 261:12384/1986.
Uzumaki et al., "Characterization of Receptor for Granulocyte Colony-Stimulating Factor on Human Circulating Neutrophils," Bio. Biophys. Res. Commun. 156:1026, 1988.
Park et al., "Interleukin-3 GM-CSF, and G-CSF Receptor Expression on Cell Lines and Primary Leukemia Cells: Receptor Heterogeneity and Relationship to Growth Factor Responsiveness," Blood 74:56, 1989.
Uzumaki et al., "Identification and Characterization of Receptors for Granulocyte Colony-Stimulating Factor on Human Placenta and Trophoblastic Cells," Proc. Natl. Acad. Sci. USA 86:9323.
Okayama and Berg, "High-Efficiency Cloning of Full-Length cDNA," Mol. Cell. Biol. 2:161, 1982.
Okayama and Berg, "A cDNA Cloning Vector that Permits Expression of cDNA Inserts in Mammalian Cells," Mol. Cell. Biol. 3:280, 1983.
Aruffo and Seed, "Molecular Cloning of a CD2S cDNA by a High-Efficiency COS Cell Expression System," Proc. Natl. Acad. Sci. USA 84:8573, 1987.
Yamasaki et al., "Cloning and Expression of the Human Interleukin-6 (BSF-2/IFN-beta 2) Receptor," Science 241:825, 1988.
Sims et al., "cDNA Expression Cloning of the IL-1 Receptor, a Member of the Immunoglobulin Superfamily," Science 241:585, 1988.

Primary Examiner—Marianne Porta Allen
Attorney, Agent, or Firm—Patricia Anne Perkins; Christopher L. Wight; Scott G. Hallquist

[57] ABSTRACT

Mammalian granulocyte-colony stimulating factor (G-CSF) receptor proteins, DNAs and expression vectors encoding mammalian G-CSF receptors, and processes for producing mammalian G-CSF receptors as products of recombinant cell culture, are disclosed.

16 Claims, 5 Drawing Sheets

FIG. 1

```
-15  XXX XXX XXX XXX XTG GAC TGC AGC TGG TTT CAG GAA CTT CTC TTG ACG AGA AGA GAG ACC AAG GAG GCC AAG CAG GGG CTG GGC CAG       74
                    XTG Asp Cys Ser Trp Phe Gln Glu Leu Leu Leu Thr Arg Arg Arg Glu Thr Lys Glu Ala Lys Gln Gly Leu Gly Gln

75  AGG TGC CAA CAT GGG GAA ACT GAG GCT CGG CTC GGA AAG GTG AAG CTT GTC CAA GAT CAC AAA GCT GGT GAA CAT CAA GGG CTG GGT GCT      164
     Arg Cys Gln His Gly Glu Thr Glu Ala Arg Leu Gly Lys Val Lys Leu Val Gln Asp His Lys Ala Gly Glu His Gln Gly Leu Gly Ala      6

165  ATG GCA AGG CTG GGA AAC TGC AGC CTG ACT TGG GCT CTG ATC ATC CTG CTC TTG CCC GGA AGT CTG GAG GAG TGC CAC ATC AGT              254
-23  Met Ala Arg Leu Gly Asn Cys Ser Leu Thr Trp Ala Leu Ile Ile Leu Leu Leu Pro Gly Ser Leu Glu Glu Cys His Ile Ser              6

255  GTC TCA GCC CCC ATC GTC CAC CTG GGG GAT CCC ATC ACA GCC TCC TGC ATC ATC AAG CAG AAC TGC AGC CAT CTG GAC CCG GAG CCA CAG      344
 7   Val Ser Ala Pro Ile Val His Leu Gly Asp Pro Ile Thr Ala Ser Cys Ile Ile Lys Gln Asn Cys Ser His Leu Asp Pro Glu Pro Gln      36

345  ATT CTG TGG AGA CTG GGA GCA GAG CTT CAG CCC TTT CTC TCC TGC ATC CAG CGT CTG TCT GAT CAG CAG ACC ATC ATC ACC CTG CCC          434
 37  Ile Leu Trp Arg Leu Gly Ala Glu Leu Gln Pro Phe Leu Ser Cys Ile Gln Arg Leu Ser Asp Gln Gln Thr Ile Ile Thr Leu Pro          66

435  CAC CTC AAC CAC ACT CAG GCC ATA CCC CAC AAC CTC TGC TCC TGC AAC TGG GGC AAC AGC CTG CAG GTT GAG CTG CGC GCA GGC              524
 67  His Leu Asn His Thr Gln Ala Ile Pro His Asn Leu Cys Ser Cys Asn Trp Gly Asn Ser Leu Gln Val Glu Leu Arg Ala Gly              96

525  TAC CCT CCA ATA CCC AGC TTC ACT CTG AAG AGT TTC AAG AGC CTC ATC TGC AGG GAC TCC ATC CTG GAG GAA CCT GAG ACC                  614
 97  Tyr Pro Pro Ile Pro Ser Phe Thr Leu Lys Ser Phe Lys Ser Leu Ile Cys Arg Asp Ser Ile Leu Glu Glu Pro Gly Pro Thr              126

615  CAC CCC ACC AGC TTC ACT CTG AAG AGT TTC AAG AGC CTC ATC TGC AGG GAC TCC ATC CTG GAC TGC GTG CCC AAG                          704
127  His Pro Thr Ser Phe Thr Leu Lys Ser Phe Lys Ser Leu Ile Cys Arg Asp Ser Ile Leu Asp Cys Val Pro Lys                          156

705  GAC GGG CAG AGC CAC TGC ATC CCA CGC AAA CAC CTG CTG TTG TAC CAG AAT ATG GGC ATC TGG GTG CAG GCA GAG AAT GCG CTG GGG          794
157  Asp Gly Gln Ser His Cys Ile Pro Arg Lys His Leu Leu Leu Tyr Gln Asn Met Gly Ile Trp Val Gln Ala Glu Asn Ala Leu Gly          186

795  ACC AGC ATG TCC TGT CTT GAT CCC ATG GTT GTG GAT CCC CCG ATG CTG CGG GAG CCC ATG GAC CCT AGC GAA                              884
187  Thr Ser Met Ser Cys Leu Asp Pro Met Val Val Asp Pro Pro Met Leu Arg Glu Pro Met Asp Pro Ser Glu                              216
```

```
885  GCG GCC CCT CAG GCA GGC TGC CTA CAG CTG TGC TGG GAG CCA GGC CTG CAG CCA TGG GAG CTG CGC CAC   974
217  Ala Ala Pro Gln Ala Gly Cys Leu Gln Leu Cys Trp Glu Pro Gly Gln Pro Trp Glu Leu Arg His        246

975  AAG CCG CAG CGT GGA GAA GGG GAA GCC AGC TGG GCA CTG GCA CTC TAT GAG GCC CTT GAG CTC TGC CCA GCC  1064
247  Lys Pro Gln Arg Gly Glu Gly Glu Ala Ser Trp Ala Leu Ala Leu Tyr Glu Ala Leu Glu Leu Cys Pro Ala  276

1065 ACG GCC TAC ACC CTG CAG ATA CGC ATC CGC TGG CCT CGG CAC AGC GAC TGG ACC CTG GAG CTG AGA ACT ACC  1154
277  Thr Ala Tyr Thr Leu Gln Ile Arg Ile Arg Cys Pro Leu Pro Gly His Ser Asp Trp Thr Leu Glu Leu Arg Thr Thr  306

1155 GAA CGG GCC CCC ACT GTC GAC CTG GAC CTG GAC CTG AGG CAG CCC CAG GTG CAG CTG TTC TGG AAG CCA GTG CCC  1244
307  Glu Arg Ala Pro Thr Val Arg Leu Asp Leu Arg Gln Pro Gln Val Gln Leu Phe Trp Lys Pro Val Pro        336

1245 CTG GAG GAA GAC AGC GGA ATC CAA GGT TAT GTG TCT TGG GTT TCT TGG GTT CAA CCC TCA GGC CAG ATC CTG CCC CTC TGC AAC ACC  1334
337  Leu Glu Glu Asp Ser Gly Ile Gln Gly Tyr Val Ser Trp Val Val Gln Pro Arg Gly Gln Ala Ile Leu Pro Leu Cys Asn Thr  366

1335 ACA GAG CTC AGC TGC TTC CAC CTG GAG GCC GCC GAG GTG GCC CTT GTG GCC TAT AAC TCA GCC GGG ACC TCT CGC CCC ACC  1424
367  Thr Glu Leu Ser Cys Phe His Leu Pro Ser Glu Ala Gln Leu Val Ala Tyr Asn Ser Ala Gly Thr Ser Arg Pro Thr  396

1425 CCG GTG GTC TTC TCA GAA AGC AGA GGC CCA ATG GCT CTC CAT GCC ATG GCC CGA GAC CCT CAC AGC CTC TGG GTA GGC TGG GAG  1514
397  Pro Val Val Phe Ser Glu Ser Arg Gly Pro Ala Leu His Ala Met Ala Arg Asp Pro His Ser Leu Trp Val Gly Trp Glu  426

1515 CCC CCC AAT CCA CCT CCT CAG TGG ATT GTG ATT GAG GAG GCG AGC CCC CCT AAT AGC AAG ACC TGG AGG ATG GAA  1604
427  Pro Pro Asn Pro Pro Pro Gln Trp Ile Val Ile Glu Glu Ala Ser Pro Pro Asn Ser Lys Thr Trp Arg Met Glu  456

1605 CAG AAT GGG AGA ACG GCC AGG CTC TAT GAG ATC ATC GTG ACT CCC TTG TAC CAG GAC  1694
457  Gln Asn Gly Arg Thr Ala Arg Leu Tyr Glu Ile Ile Val Thr Pro Leu Tyr Gln Asp  486

1695 ACC ATG GGA CCC TCC CAG CAG TCC CAT GCC CCA GAG CTG CAT CTA AAG CAC ATT GGC AAG  1784
487  Thr Met Gly Pro Ser Gln Gln Ser His Ala Pro Glu Leu His Leu Lys His Ile Gly Lys  516
```

```
1785 ACC TGG GCA CAG CTG GAG TGG GTG CCT GAG CCC CCT GAG AGC CCC CTT ACC ATC TTC TGG ACC AAC GCT CAG 1874
517  Thr Trp Ala Gln Leu Glu Trp Val Pro Glu Pro Pro Glu Ser Pro Leu Thr Ile Phe Trp Thr Asn Ala Gln 546

1875 AAC CAG TCC TTC TCC GCC ATC CTG AAT GCC CTG CTC CAT GGC TTT GTC CGT TAT CAC ATC AGT CTG CAC CTC 1964
547  Asn Gln Ser Phe Ser Ala Ile Leu Asn Ala Leu Leu His Gly Phe Val Arg Tyr His Ile Ser Leu His Leu 576

1965 ATG GCT GCC AGC CAG GCT GGG GCC ACC AGT ACA GTC CTC ATG ACC TTG ACC CCA GAG TCG GAG CTA CAC ATC CTG 2054
577  Met Ala Ala Ser Gln Ala Gly Ala Thr Ser Thr Val Leu Met Thr Leu Thr Pro Glu Ser Glu Leu His Ile Leu 606

2055 GGC CTG TTC GGC CTC CTG TTG CTC CTC ACC TGC TGT TGG ACT GCC TGG CTC TGT AGC CCC AAC AGG AAG AAT CCC CTC TGG CCA 2144
607  Gly Leu Phe Gly Leu Leu Leu Leu Leu Thr Cys Cys Trp Thr Ala Trp Leu Cys Ser Pro Asn Arg Lys Asn Pro Leu Trp Pro 636

2145 AGT GCT CAC GAC CCA GCT CAC AGC AGC CTG GGC TCC TGG GTG GTG CCC ACA ATC ATG GAG GAG GAT GCC TTC CAG CTG CCC GGC CTT GGC ACG 2234
637  Ser Ala His Asp Pro Ala His Ser Ser Leu Gly Ser Trp Val Val Pro Thr Ile Met Glu Glu Asp Ala Phe Gln Leu Pro Gly Leu Gly Thr 666

2235 CCA CCC ATC ACC AAG CTC ACA GTG CTG GAG GAG GAT GAA AAG CCG GTG AAG CTG CCC TGG GAG TCC CAT AAC AGC TCA GAG ACC TGT GGC CTC 2324
667  Pro Pro Ile Thr Lys Leu Thr Val Leu Glu Glu Asp Glu Lys Pro Val Lys Leu Pro Trp Glu Ser His Asn Ser Ser Glu Thr Cys Gly Leu 696

2325 CCC ACT CTG GTC CAG ACC TAT GTG CTC CAG GGG GAC GTT TCC ACC CAG CCC CAA TCC CAG CCT GGC ACC AGC GAT CAG GCT 2414
697  Pro Thr Leu Val Gln Thr Tyr Val Leu Gln Gly Asp Val Ser Thr Gln Pro Gln Ser Gln Pro Gly Thr Ser Asp Gln Ala 726

2415 GGG CCT CCC AGG CGA TCT GCA TAC TTT AAG GAC ATC ATG CTC CAT CCA GCC CAT GGC CTT TTG TGC TTG TTT CCT ATA ACT 2504
727  Gly Pro Pro Arg Arg Ser Ala Tyr Phe Lys Asp Ile Met Leu His Pro Ala Pro Asn Gly Leu Leu Cys Leu Phe Pro Ile Thr 756

2505 TCA GTA TTG TAA ACT AGT TTG TGG TTT GCA AAA AAA AAA 2546
757  Ser Val Leu End                                     770
```

FIG. 2C

```
2409 CAG GTC CTT TAT GGG CAG CTG CTG GGC AGC CCC ACA AGC CCA GGG CCA GGG CAC TAT CTC CGT GTG ACT CCA CTC AGC CCC TCT TGG CGG 2498
 725 Gln Val Leu Tyr Gly Gln Leu Leu Gly Ser Pro Thr Ser Pro Gly Pro Gly His Tyr Leu Arg Val Thr Pro Leu Ser Pro Ser Trp Arg  754

2499 GCC TCA CCC CCA GCC CCA AGT CCT ATG AGA ACC TCT GGT TCC AGG CCA GCC TGG TAA CCC CAG CCC CAA GCC AGG AGG 2588
 755 Ala Ser Pro Pro Ala Pro Ser Pro Met Arg Thr Ser Gly Ser Arg Pro Ala Pro Trp End                          784

2589 ACG ACT GTG TCT TTG GGC CAC TGC TCA ACT TCC CCC TCC TGC TAG GGG ATC CGG GTC CAT GGG ATG GAG GCG CTG GGG AGC CCC TAG GGC 2678

2679 TTC CTG GGG TTC CCT TCT TGG GCC TGC CTT TTA AAG GCC TGA GCT AGC TGG AGA AGA GGG GAG GGT CCA TAA GCC CAT GAC TAA AAA CTA 2768

2769 CCC CAG CCC AGG CTC TCA CCA TCT CCA GTC ACC AGC ATC TCC CTC TCC CGA ATC TCC ATA GGC TGG GCC TCC CAG GCG ATC TGC ATA 2858

2859 CTT TAA GGA CCA GAT CAT GCT CCA TCC AGC CCC ACC CAA TGG CCT TTT GTG CTT GTT TCC TAT AAC TTC AGT ATT 2933
```

FIG. 3

DNA SEQUENCES ENCODING GRANULOCYTE-COLONY STIMULATING FACTOR RECEPTORS

CROSS-REFERENCE TO RELATED APPLICATION

This application is a continuation of U.S. application Ser. No. 07/587,329, filed Sep. 24, 1990, now abandoned, which is a continuation-in-part of U.S. application Ser. No. 522,952, filed Apr. 3, 1990, which is a continuation-in-part of U.S. application Ser. No. 416,306, filed Oct. 3, 1989, which is a continuation-in-part of U.S. application Ser. No. 412,816, filed on Sep. 26, 1989, all now abandoned.

BACKGROUND OF THE INVENTION

The present invention relates generally to cytokine receptors and more specifically to granulocyte-colony stimulating factor receptors.

Human Granulocyte-Colony Stimulating Factor (G-CSF) is a lineage-specific hematopoietic protein which stimulates the proliferation and differentiation of granulocyte-committed progenitor cells. Human G-CSF has also been shown to functionally activate mature neutrophils. The cDNAs for human (Nagata et al., Nature 319;415, 1986) and mouse G-CSF (Tsuchiya et al., PNAS 83, 7633, 1986) have been isolated, permitting further structural and biological characterization of G-CSF.

G-CSF initiates its biological effect on cells by binding to specific G-CSF receptor protein expressed on the plasma membrane of a G-CSF responsive cell. Because of the ability of G-CSF to specifically bind G-CSF receptor (G-CSFR), purified G-CSFR compositions will be useful in diagnostic assays for G-CSF, as well as in raising antibodies to G-CSF receptor for use in diagnosis and therapy. In addition, purified G-CSF receptor compositions may be used directly in therapy to bind or scavenge G-CSF, thereby providing a means for regulating the immune activities of this cytokine. In order to study the structural and biological characteristics of G-CSFR and the role played by G-CSFR in the responses of various cell populations to G-CSF or other cytokine stimulation, or to use G-CSFR effectively in therapy, diagnosis, or assay, purified compositions of G-CSFR are needed. Such compositions, however, are obtainable in practical yields only by cloning and expressing genes encoding the receptors using recombinant DNA technology. Efforts to purify the G-CSFR molecule for use in biochemical analysis or to clone and express mammalian genes encoding G-CSFR have been impeded by lack of a suitable source of receptor protein or mRNA. Prior to the present invention, no cell lines were known to express high levels of G-CSFR constitutively and continuously, which precluded purification of receptor for sequencing or construction of genetic libraries for direct expression cloning.

SUMMARY OF THE INVENTION

The present invention provides DNA sequences encoding mammalian granulocyte-colony stimulating factor receptors (G-CSFR) or subunits thereof. Preferably, such DNA sequences are selected from the group consisting of (a) cDNA clones having a nucleotide sequence derived from the coding region of a native G-CSFR gene; (b) DNA sequences which are capable of hybridization to the cDNA clones of (a) under moderately stringent conditions and which encode biologically active G-CSFR molecules; and (c) DNA sequences which are degenerate as a result of the genetic code to the DNA sequences defined in (a) and (b) and which encode biologically active G-CSFR molecules. The present invention also provides recombinant expression vectors comprising the DNA sequences defined above, recombinant G-CSFR molecules produced using the recombinant expression vectors, and processes for producing the recombinant G-CSFR molecules using the expression vectors.

The present invention also provides isolated or purified protein compositions comprising mammalian G-CSFR. Preferred G-CSFR proteins are soluble forms of the native receptors.

The present invention also provides compositions for use in therapy, diagnosis, assay of GoCSFR, or in raising antibodies to G-CSFR, comprising effective quantities of soluble native or recombinant receptor proteins prepared according to the foregoing processes. These and other aspects of the present invention will become evident upon reference to the following detailed description.

BRIEF DESCRIPTION OF THE DRAWINGS

FIGS. 2A–C depicts that cDNA sequence of clone D-7 which was isolated from a human placental library, and the predicted amino acid sequence of this clone. The coding region of the predicted mature full-length membrane-bound protein from clone D7 is defined by amino acids 1–759. The predicted N-terminal Glu of the mature protein is designated amino acid number 1 and is underlined. The putative transmembrane region at amino acids 604–629 is also underlined.

DETAILED DESCRIPTION OF THE INVENTION

Definitions

Figure 1:
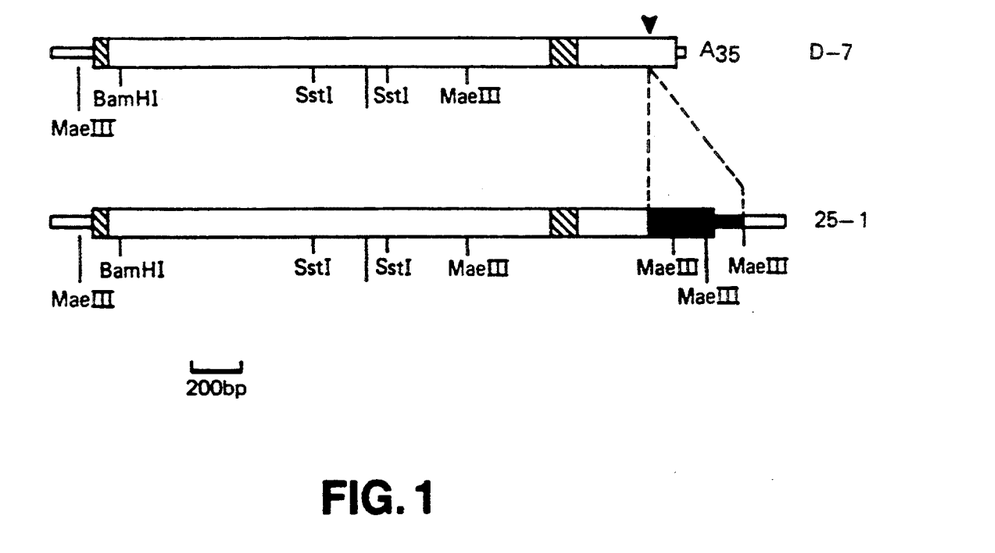
FIG. 1 shows restrictions maps of cDNA clones D-7 and 25-1 containing regions encoding human G-CSFR proteins.
Figure 2A:
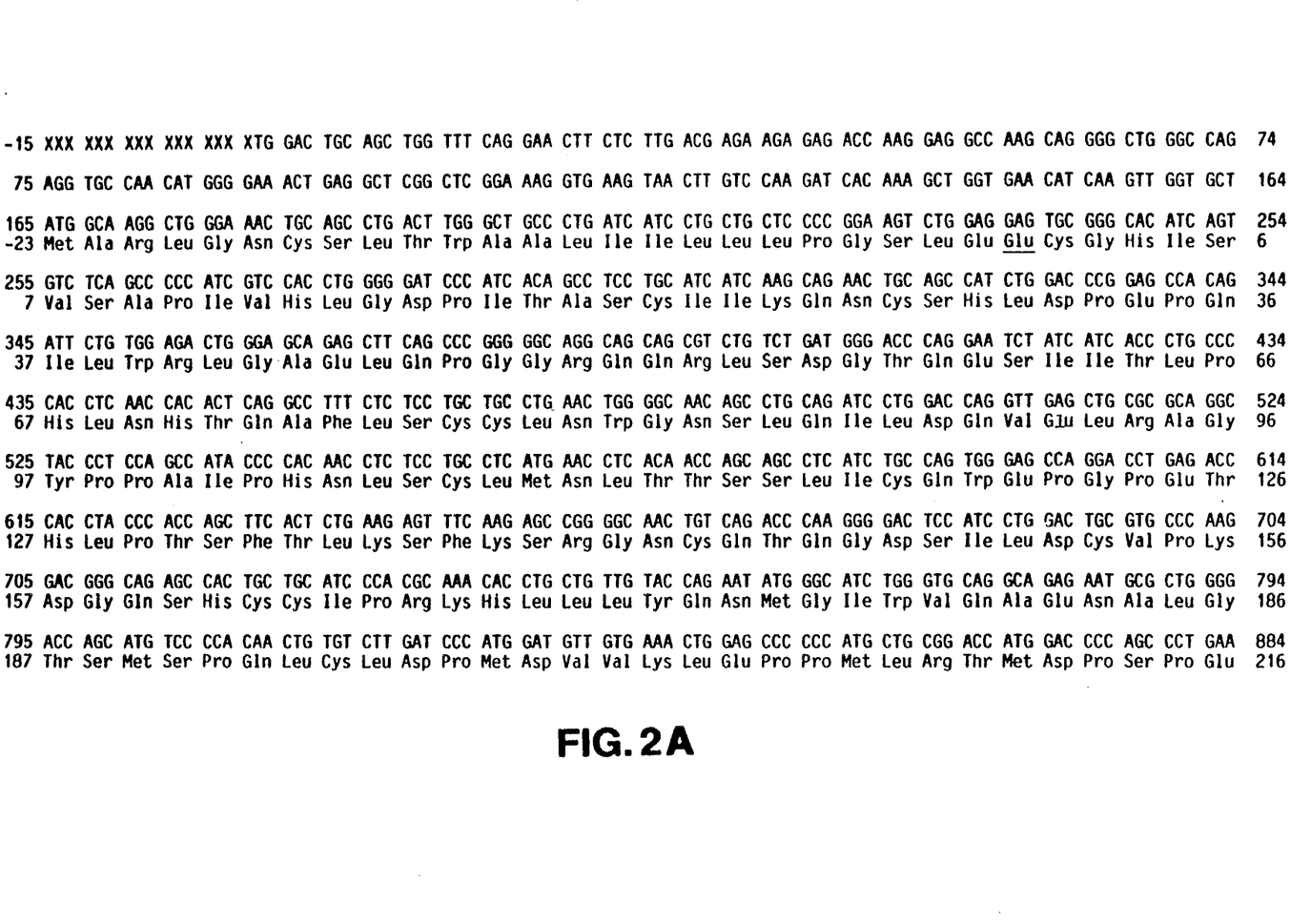
Figure 3:
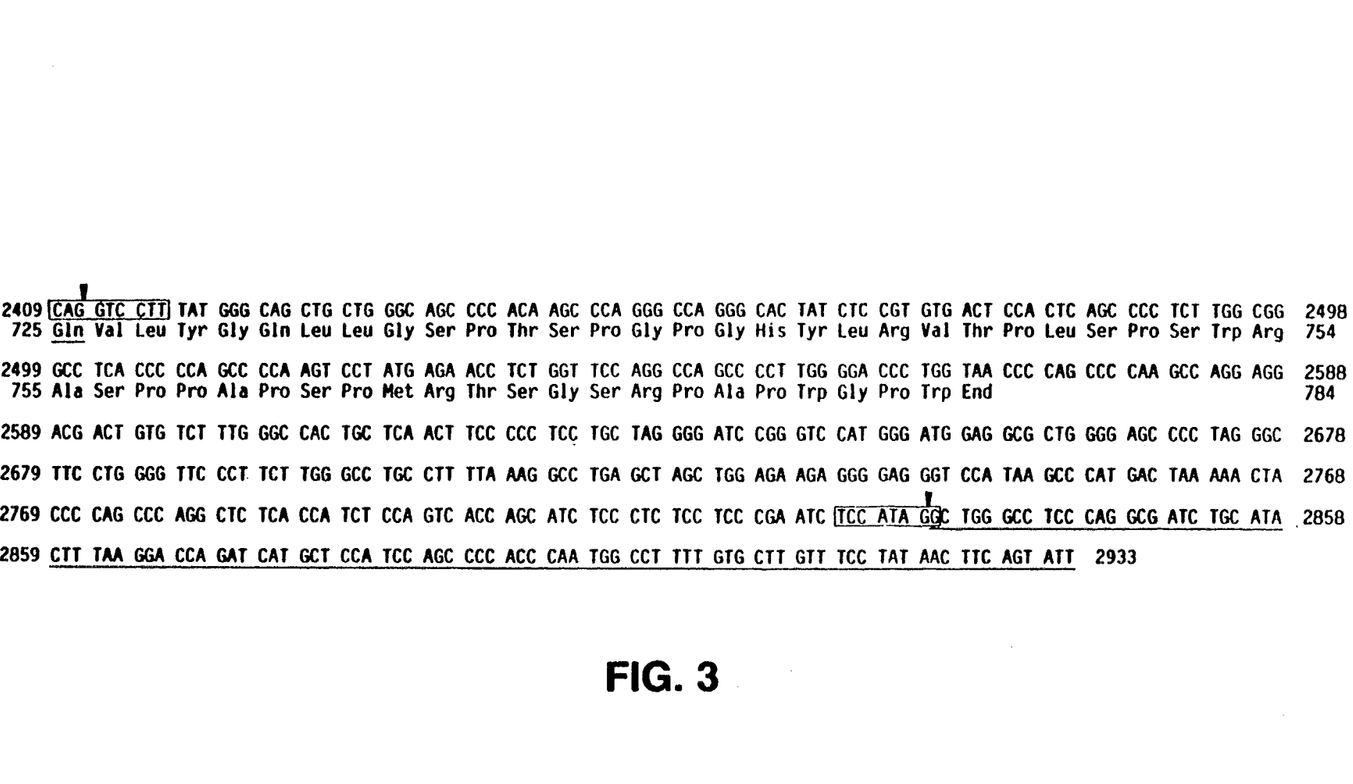
FIG. 3 depicts the 3' nucleotide sequence and predicted C-terminal amino acid sequence of clone 25-1, which is the result of an alternative splicing arrangement. The position of the intron insertion in clone 25-1 is indicated at with a ▼ after nucleotide 2411 of FIG. 1. The position of the intron-exon boundaries are indicated with a ▼, and splice-donor and splice-acceptor recognition sequences are boxed. Sequences also present in clone D-7 are underlined.

G-CSF is a growth factor which induces growth and differentiation of neutrophilic granulocyte progenitors. The biological activities of G-CSF are mediated through binding to specific cell surface receptors, referred to as "G-CSF receptors" or "G-CSFR". G-CSFR, as used herein, refers to proteins having amino acid sequences which are substantially similar to native mammalian G-CSFR amino acid sequences, such as the human G-CSFR sequence disclosed in FIG. 1, or fragments thereof, and which are biologically active as defined below, in that they are capable of binding G-CSF molecules or, in their native configuration as intact human plasma membrane proteins, transducing a biological signal initiated by a G-CSF molecule binding to a cell, or cross-reacting with anti-G-CSFR antibodies raised against G-CSFR from natural (i.e., nonrecombinant) sources. Specific embodiments of G-CSFR include polypeptides substantially equivalent to the sequence of amino acids 1-759 of FIGS. 2A–C (clone D-7) or the sequence of amino acids 1-776 of the protein encoded by clone 25-1 as disclosed in FIGS. 2A–C and 3. The terms "G-CSF receptor" or "G-CSFR" include, but are not limited to, soluble G-CSF receptors, as defined below. As used throughout this specification, the term "mature" means a protein expressed in a form lacking a leader sequence as may be present in full-length transcripts of a native gene. Various bioequivalent protein and amino acid analogs are described in detail below.

The mature N-terminal amino acid is predicted to be Glu $^1$ (underlined and designated as amino acid 1 in FIGS. 2A–C), based on the algorithm of von Heijne, G., *Nucl. Acids Res.* 4:4683 (1986), for determining signal cleavage sites. However, several factors suggest that Ser$^{-3}$ may be the correct mature N-terminal amino acid, based on the observation that Ser$^{-3}$ is 21 amino acids from the N-terminal Met and is preceded by the small amino acid residue Gly, both of which are accepted criteria for identifying signal cleavage sites. The actual N-terminal amino acid of the mature protein can be confirmed by sequencing purified G-CSFR protein using standard techniques. Thus, amino acid sequences equivalent to those described above include, for example, amino acids −3 through 759 of FIGS. 2A–C (clone D-7) or −3 through 776 of the protein encoded by clone 25-1 as disclosed in FIGS. 2A–C and 3.

In their native configuration, receptor proteins are present as intact human plasma membrane proteins having an extracellular region which binds to a ligand, a hydrophobic transmembrane region which causes the protein to be immobilized within the plasma membrane lipic bilayer, and a cytoplasmic or intracellular region which interacts with cytoplasmic proteins and/or chemicals to deliver a biological signal to effector cells via a cascade of chemical reactions within the cytoplasm of the cell. The hydrophobic transmembrane region and a highly charged sequence of amino acids in the cytoplasmic region immediately following the transmembrane region cooperatively function to halt transport of the G-CSFR across the plasma membrane. "Soluble G-CSFR" or sG-CSFR", as used in the context of the present invention, refer to a protein, or a substantially equivalent analog, having an amino acid sequence corresponding to the extracellular region of native G-CSFR, for example polypeptides having the amino acid sequences substantially equivalent to the sequences of amino acids 1-603 of FIGS. 2A–C. Equivalent sG-CSFRs include polypeptides which vary from the sequences shown in FIGS. 2A–C by one or more substitutions, deletions, or additions, and which retain the ability to bind G-CSF and inhibit the ability of G-CSF to transduce a signal via cell surface bound G-CSF receptor proteins. Because sG-CSFR proteins are devoid of a transmembrane region, they are secreted from the host cell in which they are produced. Equivalent soluble G-CSFR include, for example, the sequence of amino acids −3 through 603 of FIGS. 2A–C. When administered in therapeutic formulations, sG-CSFR proteins circulate in the body and bind to circulating G-CSF molecules, preventing interaction of G-CSF with natural G-CSF receptors and inhibiting transduction of G-CSF-mediated biological signals, such as immune or inflammatory responses. The ability of a polypeptide to inhibit G-CSF signal transduction can be determined by transfecting cells with recombinant G-CSF receptor DNAs to obtain recombinant receptor expression. The cells are then contacted with G-CSF and the resulting metabolic effects examined. If an effect results which is attributable to the action of the ligand, then the recombinant receptor has signal transducing activity. Examplary procedures for determining whether a polypeptide has signal transducing activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986); and Chou et al., *J. Biol. Chem.* 262:1842 (1987). Alternatively, primary cells of cell lines which express an endogenous G-CSF receptor and have a detectable biological response to G-CSF could also be utilized.

"Substantially similar" G-CSFR include those whose amino acid or nucleic acid sequences vary from a reference sequence by one or more substitutions, deletions, or additions, the net effect of which is to retain biological activity of the G-CSFR protein. Alternatively, nucleic acid subunits and analogs are "substantially similar" to the specific DNA sequences disclosed herein if: (a) the DNA sequence is derived from the coding region of a native mammalian G-CSFR gene; (b) the DNA sequence is capable of hybridization to DNA sequences of (a) under moderately stringent conditions and which encode biologically active G-CSFR molecules; or DNA sequences which are degenerate as a result of the genetic code to the DNA sequences defined in (a) or (b) and which encode biologically active G-CSFR molecules. Substantially similar analog proteins will be greater than about 30 percent similar to the corresponding sequence of the native G-CSFR. Sequences having lesser degrees of similarity but comparable biological activity are considered to be equivalents. More preferably, the analog proteins will be greater than about 80 percent similar to the corresponding sequence of the native G-CSFR, in which case they are defined as being "substantially identical." In defining nucleic acid sequences, all subject nucleic acid sequences capable of encoding substantially similar amino acid sequences are considered substantially similar to a reference nucleic acid sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, ed., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of G-CSF receptors, means that a particular molecule shares sufficient amino acid sequence similarity with the embodiments of the present invention disclosed herein to be capable of binding detectable quantities of G-CSF, transmitting a G-CSF stimulus to a cell, for example, as a component of a hybrid receptor construct, or cross-reacting with anti-G-CSFR antibodies raised against G-CSFR from natural (i.e., nonrecombinant) sources. Preferably, biologically active G-CSF receptors within the scope of the present invention are capable of binding greater than 0.1 nmoles G-CSF per nmole receptor, and most preferably, greater than 0.5 nmole G-CSF per nmole receptor in standard binding assays (see below).

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention can be assembled from eDNA fragments and short oligonucleotide linkers, or from a series of oligonucleotides, to provide a synthetic gene which is capable of being expressed in a recombinant transcriptional unit.

"Recombinant expression vector" refers to a replicable DNA construct used either to amplify or to express DNA which encodes G-CSFR and which includes a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

The term "isolated", as used in the context of this specification to define the purity of a G-CSFR or sG-CSFR protein or protein composition, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. G-CSFR or sG-CSFR is isolated if it is detectable as a single protein band in a polyacrylamide gel by silver staining.

Isolation of cDNAs Encoding G-CSFR

The coding sequence of a mammalian G-CSFR is obtained by first isolating a cDNA sequence encoding G-CSFR from a recombinant DNA library generated using either genomic DNA or cDNA. The preferred method for constructing a eDNA library is to prepare polyadenylated mRNA obtained from a particular cell line which expresses a mammalian G-CSFR and converting the polyadenylated RNA to cDNA by reverse transcription. A particularly preferred cellular source of mRNA for construction of the cDNA library is human placental RNA.

A cDNA library will contain G-CSFR sequences which can be readily identified by screening the library with an appropriate nucleic acid probe which is capable of hybridizing with G-CSFR cDNA. Such probes can be derived from the nucleotide sequences disclosed herein. Alternatively, DNAs encoding G-CSFR proteins can also be assembled by ligation of synthetic oligonucleotide subunits to provide a complete coding sequence.

The cDNAs encoding G-CSFR of the present invention were isolated by the method of direct expression cloning. Specifically, a cDNA library was constructed by first isolating cytoplasmic mRNA from human placental tissue using standard techniques. Polyadenylated mRNA was isolated and used to prepare double-stranded cDNA. Purified cDNA fragments were then ligated into psfCAV vector DNA described in detail below in Example 2. The psfCAV vectors containing the G-CSFR cDNA fragments were transformed into *E. coli* strain DH5α. Transformants were plated to provide approximately 800 colonies per plate. The resulting colonies were harvested and each pool used to prepare plasmid DNA for transfection into COS-7 cells essentially as described by Cosman et al. (*Nature* 312:768, 1984) and Luthman et al. (*Nucl. Acid Res.* 11:1295, 1983). Transformants expressing biologically active cell surface G-CSF receptors were identified by screening for the ability of G-CSFR to bind $^{125}$I-G-CSF ($5 \times 1^{-10}$M). Specifically, transfected COS-7 cells were incubated with medium containing $^{125}$I-G-CSF, the cells washed to remove unbound labeled G-CSF, and the cell monolayers contacted with X-ray film to detect concentrations of G-CSF binding, as disclosed by Sims et al, *Science* 241:585 (1988). Transfectants detected in this manner appear as dark foci against a relatively light background.

This approach as used to screen approximately 30,000 cDNAs in pools of approximately 600 cDNAs until assay of a transfectant pool indicated positive foci for G-CSF binding. A frozen stock of bacteria from this positive pool was grown in culture and plated to provide individual colonies, which were screened until single clones were identified which are capable of directing synthesis of a surface protein with detectable G-CSF binding activity. Additional cDNA clones can be isolated from cDNA libraries of other mammalian species by cross-species hybridization of human G-CSFR cDNAs with cDNA derived from other mammalian species. For use in hybridization, DNA encoding G-CSFR may be covalently labeled with a detectable substance such as a fluorescent group, a radioactive atom or a chemiluminescent group by methods well known to those skilled in the art. Such probes could also be used for in vitro diagnosis of particular conditions.

Like most mammalian genes, mammalian G-CSF receptors are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Proteins and Analogs

The present invention provides isolated recombinant mammalian G-CSFR polypeptides as defined above. Isolated G-CSFR polypeptides are substantially free of other contaminating materials of natural or endogenous origin and contain less than about 1% by mass of protein contaminants residual of production processes. Such polypeptides are optionally without associated native-pattern glycosylation. Mammalian G-CSFR of the present invention includes, by way of example, primate, human, murine, canine, feline, bovine, ovine, equine and, porcine G-CSFR. Derivatives of G-CSFR within the scope of the invention also include various structural forms of the primary protein which retain biological activity. Due to the presence of ionizable amino and carboxyl groups, for example, a G-CSFR protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to G-CSFR amino acid side chains or at the N- or C-termini. Other derivatives of G-CSFR within the scope of this invention include covalent or aggregative conjugates of G-CSFR or its fragments with other proteins or polypeptides, such as by synthesis in recombinant culture as N-terminal or C-terminal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast co-factor leader). G-CSFR protein fusions can comprise peptides added to facilitate purification or identification of G-CSFR (e.g., poly-His). The amino acid sequence of G-CSF receptor can also be linked to the peptide Asp-Tyr-Lys-Asp-Asp-Asp-Asp-Lys (DYKDDDDK) (Hopp et al., *Bio/Technology* 6: 1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli.*

G-CSFR derivatives may also be used as immunogens, reagents in receptor-based immunoassays, or as binding agents for affinity purification procedures of G-CSF or other binding ligands. G-CSFR derivatives may also be obtained by cross-linking agents, such as M-maleimidobenzoyl succinimide ester and N-hydroxysuccinimide, at cysteine and lysine residues. G-CSFR proteins may also be covalently bound through reactive side groups to various insoluble substrates, such as cyanogen bromide-activated, hisoxirane-activated, carbonyldiimidazole-activated or tosyl-activated agarose structures, or by adsorbing to polyolefin surfaces (with or without glutaraldehyde cross-linking). Once bound to a substrate, G-CSFR may be used to selectively bind (for purposes of assay or purification) anti-G-CSFR antibodies or G-CSF.

The present invention also includes G-CSFR with or without associated native-pattern glycosylation. G-CSFR expressed in yeast or mammalian expression systems, e.g., COS-7 cells, may be similar or slightly different in molecular weight and glycosylation pattern than the native molecules, depending upon the expression system. Expression of G-CSFR DNAs in bacteria such as *E. coli* provides non-glycosylated molecules. Functional mutant analogs of mammalian G-CSFR having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between A 1 and Z, or an amino acid other than Asn between Asn and $A_1$.

G-CSFR derivatives may also be obtained by mutations of G-CSFR or its subunits. A G-CSFR mutant, as referred to herein, is a polypeptide homologous to G-CSFR but which has an amino acid sequence different from native G-CSFR because of a deletion, insertion or substitution.

Bioequivalent analogs of G-CSFR proteins may be constructed by, for example, making various substitutions of residues or sequences or deleting terminal or internal residues or sequences not needed for biological activity. For example, aliphatic amino acid residues, such as Ile, Val, Leu or Ala may be substituted for one another, or polar amino acid residues, such as Lys and Arg, Glu and Asp, or Gln and Asn, may be substituted for one another. Also, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Subunits of G-CSFR may be constructed by deleting terminal or internal residues or sequences. Particularly preferred subunits include those in which the transmembrane region and intracellular domain of G-CSFR are deleted or substituted with hydrophilic residues to facilitate secretion of the receptor into the cell culture medium. The resulting protein is a soluble truncated G-CSFR molecule which may retain its ability to bind G-CSF.

Mutations in nucleotide sequences constructed for expression of analog G-CSFR must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed G-CSFR mutants screened for the desired activity.

Not all mutations in the nucleotide sequence which encodes G-CSFR will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Expression Of Recombinant G-CSFR

The present invention provides recombinant expression vectors which include synthetic or eDNA-derived DNA fragments encoding mammalian G-CSFR or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA fibosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a fibosome binding site is operably linked to a coding sequence if it is positioned so as to permit translation. Generally, operably linked means contiguous and, in the case of secretory leaders, contiguous and in reading frame.

DNA sequences encoding mammalian G-CSF receptors which are to be expressed in a microorganism will preferably contain no introns that could prematurely terminate transcription of DNA into mRNA; however, premature termination of transcription may be desirable, for example, where it would result in routants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to the sequences of the provided cDNA under moderately stringent conditions (50° C., 2×SSC) and other sequences hybridizing or degenerate to those which encode biologically active G-CSF receptor polypeptides.

Transformed host cells are cells which have been transformed or transfected with G-CSFR vectors constructed using recombinant DNA techniques. Transformed host cells ordinarily express G-CSFR, but host cells transformed for purposes of cloning or amplifying G-CSFR DNA do not need to express G-CSFR. Expressed G-CSFR will be deposited in the cell membrane or secreted into the culture supernatant, depending on the G-CSFR DNA selected. Suitable host cells for expression of mammalian G-CSFR include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce mammalian G-CSFR using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of G-CSFR that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coil. Bacillus subtilis, Salmonella typhimurium*, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., U.S.A.) and pCAV/NOT (ATCC Accession No. 68014. These pBR322 "backbone" sections are combined with an appropriate promoter and the structural sequence to be expressed. E. coli is typically transformed using derivatives of pBR322, a plasmid derived from an E. coli species (Bolivar et al., Gene 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and EPA 36,776) and tac promoter (Maniatis, Molecular Cloning: A Laboratory Manual, Cold Spring Harbor Laboratory, p. 412, 1982). A particularly useful bacterial expression system employs the phage $\lambda P_L$ promoter and cI857lts thermolabile repressor. Plasmid vectors available from the American Type Culture Collection which incorporate derivatives of the $\lambda P_L$ promoter include plasmid pHUB2, resident in E. coli strain JMB9 (ATCC 37092) and pPLc28, resident in E. coli RR1 (ATCC 53082).

Recombinant G-CSFR proteins may also be expressed in yeast hosts, preferably from the Saccharomyces species, such as S. cerevisiae. Yeast of other genera, such as Pichia or Kluyveromyces may also be employed. Yeast vectors will generally contain an origin of replication from the 2μ yeast plasmid or an autonomously replicating sequence (ARS), promoter, DNA encoding G-CSFR, sequences for polyadenylation and transcription termination and a selection gene. Preferably, yeast vectors will include an origin of replication and selectable marker permitting transformation of both yeast and E. coli, e.g., the ampicillin resistance gene of E. coli and S. cerevisiae trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in E. coli (Amp$^r$ gene and origin of replication) and yeast DNA sequences including a glucose-repressible ADH2 promoter and α-factor secretion leader. The ADH2 promoter has been described by Russell et al. (J. Biol. Chem. 258:2674, 1982) and Beier et al. (Nature 300:724, 1982). The yeast el-factor leader, which directs secretion of heterologous proteins, can be inserted between the promoter and the structural gene to be expressed. See, e.g., Kurjan et al., Cell 30:933, 1982; and Bitter et al., Proc. Natl. Acad. Sci. USA 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., Proc. Natl. Acad. Sci. USA 75: 1929, 1978, selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, Bio/Technology 6:47 (1988). Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273:113, 1978). Smaller or larger SV40 fragments may also be used, provided the approximately 250 bp sequence extending from the Hind IH site toward the BglI site located in the viral origin of replication is included. Further, mammalian genomic G-CSFR promoter, control and/or signal sequences may be utilized, provided such control sequences are compatible with the host cell chosen. Additional details regarding the use of a mammalian high expression vector to produce a recombinant mammalian G-CSF receptor are provided in Example 2 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

A particularly preferred eukaryotic vector for expression of G-CSFR DNA is disclosed below in Example 2. This vector, referred to as pCAV/NOT, was derived from the mammalian high expression vector pDC201 and contains regulatory sequences from SV40, adenovirus-2, and human cytomegalovirus.

Purified mammalian G-CSF receptors or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a G-CSF or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RPHPLC) steps employing hydrophobic RP-HPLC media, e.g., silica gel having pendant methyl or other aliphatic groups, can be employed to further purify a G-CSFR composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian G-CSFR can be disrupted by any convenient method, including freeze-thaw cycling, sonication, mechanical disruption, or use of cell lysing agents.

Fermentation of yeast which express mammalian G-CSFR as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Human G-CSFR synthesized in recombinant culture is characterized by the presence of non-human cell components, including proteins, in amounts and of a character which depend upon the purification steps taken to recover human G-CSFR from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of G-CSFR free of proteins which may be normally associated with G-CSFR as it is found in nature in its species of origin, e.g. in cells, cell exudates or body fluids.

G-CSFR compositions are prepared for administration by mixing G-CSFR having the desired degree of purity with physiologically acceptable carders. Such carriers will be nontoxic to recipients at the dosages and concentrations employed. Ordinarily, the preparation of such compositions entails combining the G-CSFR with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients.

G-CSFR compositions may be used to attenuate G-CSF-mediated immune responses. To achieve this result, a therapeutically effective quantity of a G-CSFR composition is administered to a mammal, preferably a human, in association with a pharmaceutical carrier or diluent.

The following examples are offered by way of illustration, and not by way of limitation.

EXAMPLES

Example 1

Binding Assays

A. Radiolabeling of G-CSF. Recombinant human G-CSF, in the form of a fusion protein containing a hydrophilic octapeptide at the N-terminus, was expressed in yeast as a secreted protein and purified by affinity chromatography as described by Hopp et al., *Bio/Technology* 6: 1204, 1988. The protein was radiolabeled using the commercially available solid phase agent, IODO-GEN (Pierce). In this procedure, 5 μg of IODO-GEN were plated at the bottom of a 10×75 mm glass tube and incubated for 20 minutes at 4° C. with 75 μl of 0.1M sodium phosphate, pH 7.4 and 20 μl (2 mCi) Na $^{125}$I. This solution was then transferred to a second glass tube containing 5 μg G-CSF in 45 μl PBS for 20 minutes at 4° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-G-CSF was diluted to a working stock solution of $1 \times 10^{-7}$M in binding medium and stored for up to one month at 4° C. without detectable loss of receptor binding activity. The specific activity is routinely $1 \times 10^{16}$ cpm/mmole G-CSF. Radiolabeled G-CSF is used as described below to assay for G-CSF receptors.

B. Membrane Binding Assays. Human placental membranes were incubated at 4° C. for 2 hr with $^{125}$I-G-CSF in binding medium, 0.1% bacitracin, 0.02% aprotinin, and 0.4% BSA in a total volume of 1.2 ml. Control tubes containing in addition a 100×molar excess of unlabeled G-CSF were also included to determine nonspecific binding. The reaction mixture was then centrifuged at 15,000×g in a microfuge for 5 minutes. Supernatants were discarded, the surface of the membrane pellets carefully rinsed with ice-cold binding medium, and the radioactivity counted on a gamma counter. Using this assay, it was determined that the G-CSFR present in the COS cell supernatants of Example 2 had a $K_a$ of about $1 \times 10^9 M^{-1}$ and a molecular weight of about 35 kDa.

C. Solid Phase Binding Assays. The ability of G-CSFR to be stably adsorbed to nitrocellulose from detergent extracts of human cells yet retain G-CSF-binding activity provided a means of detecting G-CSFR. Cells extracts were prepared by mixing a cell pellet with a 2× volume of PBS containing 1% Triton X-100 and a cocktail of protease inhibitors (2 mM phenylmethyl sulfonyl fluoride, 10 μM pepstatin, 10 μM leupeptin, 2 mM o-phenanthroline and 2 mM EGTA) by vigorous vortexing. The mixture was incubated on ice for 30 minutes after which it was centrifuged at 12,000× g for 15 minutes at 8° C. to remove nuclei and other debris. Two microliter aliquots of cell extracts were placed on dry BA85/21 nitrocellulose membranes (Schleicher and Schuell, Keene, N.H.) and allowed to dry. The membranes were incubated in tissue culture dishes for 30 minutes in Tris (0.05M) buffered saline (0.15M) pH 7.5 containing 3% w/v BSA to block nonspecific binding sites. The membrane was then covered with 0.3 nM $^{125}$I-G-CSF in PBS+3% BSA and incubated for 2 hr at 4° C. with shaking. At the end of this time, the membranes were washed 3 times in PBS, dried and placed on Kodak X-Omat AR film for 18 hr at −70° C. This assay was performed to detect the presence of G-CSFR in various cells lines and tissue sources.

D. Binding Assay for Soluble G-CSFR. Soluble G-CSFR present in COS-7 cell supernatants are measured by inhibition of $^{125}$I-CSF binding to a G-CSF-dependent cell line, or any other human cell or cell line expressing G-CSF receptors, such as as human placental cell. Supernatants are harvested from COS-7 cells 3 days after transfection, concentrated 10-fold, and preincubated with $^{125}$I-G-CSF for 1 hour at 37° C. Appropriate G-CSF-receptor-bearing cells are added to a final volume of 150 ul, incubated for an additional 30 minutes at 37° C., and assayed and analyzed as described by Park et al., *J. Biol. Chem.* 261:4177 (1986).

Example 2

Isolation of Human G-CSF R cDNAs by Direct Expression of Active Protein in COS-7 Cells A tissue source for G-CSFR was selected by screening various human cell lines and tissues for expression of G-CSFR based on their ability to bind $^{125}$I-labeled G-CSF, prepared as described above in Example 1A. Human placental membranes were found to express a reasonable number of receptors. Equilibrium binding studies were performed according to Example 1B and showed that the membrane exhibited biphasic binding of $^{125}$I-G-CSF with high affinity sites ($K_a = 4 \times 10^{19} M^{-1}$) of 0.4 pmoles receptor/mg protein.

An unsized cDNA library was constructed by reverse transcription of polyadenylated mRNA isolated from total RNA extracted from the human placental tissue (Ausubel et al., eds., *Current Protocols in Molecular Biology*, Vol. 1, 1987). The cells were harvested by lysing the tissue cells in a guanidinium isothiocyanate solution and total RNA was isolated using standard techniques as described by Maniatis, *Molecular Cloning: A Laboratory Manual*, Cold Spring Harbor Laboratory, 1982.

Polyadenylated RNA was isolated by oligo dT cellulose chromatography and double-stranded cDNA was prepared by a method similar to that of Gubler and Hoffman, *Gene* 25:263, 1983. Briefly, the polyadenylated RNA was convened to an RNA-cDNA hybrid with reverse transcriptase using oligo dT as a primer. The RNA-cDNA hybrid was then converted into double-stranded eDNA using RNAase H in combination with DNA polymerase I. The resulting double stranded eDNA was blunt-ended with T4 DNA polymerase. BglII adaptors were ligated to the 5′ ends of the resulting blunt-ended eDNA as described by Haymerle, et al., *Nuclear Acids Research*, 14: 8615, 1986. The non-ligated adaptors were removed by gel filtration chromatography at 68° C., leaving 24 nucleotide non-self-complementary overhangs on the cDNA. The same procedure was used to convert the 5′ BglII ends of the mammalian expression vector psfCAV to 24 nucleotide overhangs complementary to those added to the cDNA. Optimal proportions of adaptored vector and eDNA were ligated in the presence of T4 polynucleotide kinase. Dialyzed ligation mixtures were electroporated into *E. coli* strain DH5α and transformants selected on ampicillin plates.

The resulting cDNAs were ligated into the eukaryotic expression vector psfCAV, which was designed to express eDNA sequences inserted at its multiple cloning site when transfected into mammalian cells. psfCAV was assembled from pDC201 (a derivative of pMLSV, previously described by Cosman et al., *Nature* 312: 768, 1984), SV40 and cytomegalovirus DNA and comprises, in sequence with the direction of transcription from the origin of replication: (1) SV40 sequences from coordinates 5171–5270 containing the origin of replication, enhancer sequences and early and late promoters; (2) cytomegalovirus sequences containing the promoter and enhancer regions (nucleotides 671 to +63 from the sequence published by Boechart et al. (*Cell* 41:521, 1985); (3) adenovirus-2 sequences from coordinates 5779–6079 containing sequences for the motor late promoter and the first exon of the tripartite leader (TPL), coordinates 7101–7172 and 9634–9693 containing the second exon and part of the third exon of the TPL and a multiple cloning site (MCS) containing sites for XhoI, KpnI, SmaI andBgl/I; (4) SV40 sequences from coordinates 4127–4100 and 2770–2533 containing the polyadenylation and termination signals for early transcription; (5) with adenovirus sequences from coordinates 10532–11156 of the virus-associated RNA genes VAI and VAII of pDC201; and (6) pBR322 sequences from coordinates 4363–2486 and 1094–375 containing the ampicillin resistance gene and origin of replication.

The resulting human placental eDNA library in sfCAV was used to transform *E. coli* strain DH5α, and recombinants were plated to provide approximately 500–600 colonies per plate and sufficient plates to provide approximately 30,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al., *Nucl. Acids Res.* 11:1295 (1983) and McCutchan et al., *J. Natl. Cancer Inst.* 41:351 (1986). The cells were then grown in culture for three days to permit transient expression of the inserted sequences. After three days, cell culture supernatants were discarded and the cell monolayers in each plate assayed for G-CSF binding as follows. Three ml of binding medium containing $1.2 \times 10^{-11}$M $^{125}$I-labeled flag-G-CSF was added to each plate and the plates incubated at 4° C. for 120 minutes. This medium was then discarded, and each plate was washed once with cold binding medium (containing no labeled G-CSF) and twice with cold PBS. The edges of each plate were then broken off, leaving a flat disk which was contacted with X-ray film for 72 hours at −70° C. using an intensifying screen. G-CSF binding activity was visualized on the exposed films as a dark spot against a relatively uniform background.

After approximately 30,000 recombinants from the library had been screened in this manner, nine transfectant pools were observed to provide G-CSF binding foci which were clearly apparent against the background exposure.

A frozen stock of bacteria from the positive pool was then used to obtain plates of approximately 60 colonies. Replicas of these plates were made on nitrocellulose filters, and the plates were then scraped and plasmid DNA prepared and transfected as described above to identify a positive plate. Bacteria from individual colonies from the nitrocellulose replica of this plate were grown in 0.2 ml cultures, which were used to obtain plasmid DNA. The plasmid DNA was then transfected into COS-7 cells as described above. In this manner, a single clone, clone D-7, was isolated which was capable of inducing expression of G-CSFR in COS cells. A glycerol stock of bacteria transformed with this G-CSFR cDNA clone in the expression vector pCAV/-NOT (or pDC302) has been deposited with the American Type Culture Collection, 12301 Parklawn Drive, Rockville, Md. 20852, U.S.A., under accession number 68102 (deposited Sep. 27, 1989).

An additional cDNA clone encoding G-CSFR was isolated from the same placental library. Recombinants from the placental cDNA library were plated on *E. coli* strain DH5α and transformants selected on ampicillin plates. The transformants were screened by plaque hybridization techniques under conditions of high stringency (63° C., 0.2×SSC) using a $^{32}$P-labeled probe made from the human G-CSFR clone D-7. A hybridizing clone (clone 25-1) was isolated which is identical to clone D-7, except that it contains an intron insertion after nucleotide 2411, adding nucleotides 2412–2832 of FIG. 3 and resulting in a change in reading frame and a corresponding change in amino acid sequence. The 3' nucleotide sequence and predicted C-terminal amino acid sequence of clone 25-1 are set forth in FIG. 3.

Example 3

Construction of cDNAs Encoding Soluble Human G-CSFR

Soluble human G-CSFR was cloned into the mammalian expression vector pDC302, described above, utilizing the polymerase chain reaction (PCR) technique. The following primers were used:

5' End Primer
5'-GGTACCATGGCAAGGCTGGGAAAC
Asp718 site/Initiation Codon

-continued

3' End Primer
5'-TCTAGAACTCAGCCTCGATGTG
BglII/Termination Codon

The PCR product thus contains Asp718 and BglII restriction sites at the 5' and 3' termini, respectively. These restriction sites are used to clone into pDC302. The 3' sequence is antisense relative to sequence disclosed in FIGS. 2A–C. The template for the PCR reaction is clone 25-1, described above, which contains the G-CSFR. The DNA sequences encoding the G-CSFR are then amplified by PCR, substantially as described by Innis et al., eds., PCR *Protocols: A Guide to Methods and Applications* (Academic Press, 1990). The resulting amplified clone was then isolated and ligated into pDC302 and expressed in monkey COS-7 cells as described above.

Example 4

Preparation of Monoclonal Antibodies to G-CSFR

Preparations of purified recombinant G-CSFR, for example, human G-CSFR, or transfected COS cells expressing high levels of G-CSFR are employed to generate monoclonal antibodies against G-CSFR using conventional techniques, for example, those disclosed in U.S. Pat. No. 4,411,993. Such antibodies are likely to be useful in interfering with G-CSF binding to G-CSF receptors, for example, in ameliorating toxic or other undesired effects of G-CSF, or as components of diagnostic or research assays for G-CSF or soluble G-CSF receptor.

To immunize mice, G-CSFR immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS 1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with G-CSFR, for example, by adaptations of the techniques disclosed by Engvall et al., *Immunochem.* 8:871 (1971) and in U.S. Pat. No. 4,703,004. Positive clones are then injected into the peritoneal cavities of syngeneic Balb/c mice to produce ascites containing high concentrations (>1 mg/ml) of anti-G-CSFR monoclonal antibody. The resulting monoclonal antibody can be purified by ammonium sulfate precipitation followed by gel exclusion chromatography, and/or affinity chromatography based on binding of antibody to Protein A of *Staphylococcus aureus.*

We claim:

1. An isolated DNA sequence selected from the group consisting of:
   (a) cDNA clones having a nucleotide sequence derived from the coding region of a native human G-CSFR gene selected from the group consisting of clones encoding an amino acid sequence comprising amino acids 1 through 759 of FIGS. 2A–C and clones encoding an amino acid sequence comprising amino acids 1 through 776 of FIGS. 2A–C and FIG. 3, and which encode G-CSFR molecules that exhibit biological activity in an assay selected from the group consisting of a G-CSFR membrane binding assay, a G-CSFR solid phase binding assay, a G-CSFR whole cell binding assay, and a binding assay for soluble G-CSFR;
   (b) isolated DNA sequences which encode G-CSFR molecules identical to the G-CSFR molecules encoded by the cDNA clones of (a) except for modification(s) to the amino acid sequence selected from the group consisting of: inactivated N-linked glycosylation sites; altered KEX2 protease cleavage sites; and conservative amino acid substitutions, which G-CSFR molecules exhibit biological activity in an assay selected from the group consisting of a G-CSFR membrane binding assay, a G-CSFR solid phase binding assay, a G-CSFR whole cell binding assay, and a binding assay for soluble G-CSFR; and
   (c) isolated DNA sequences which are degenerate as a result of the genetic code to the DNA sequences defined in (a) and (b) and which encode G-CSFR molecules that exhibit biological activity in an assay selected from the group consisting of a G-CSFR membrane binding assay, a G-CSFR solid phase binding assay, a G-CSFR whole cell binding assay, and a binding assay for soluble G-CSFR.

2. An isolated DNA sequence according to claim 1, encoding a soluble biologically active human G-CSFR.

3. A recombinant expression vector comprising a DNA sequence according to claim 2.

4. A host cell transformed or transfected with a recombinant expression vector according to claim 3.

5. A process for preparing a human G-CSF receptor or an analog thereof, comprising culturing a host cell according to claim 4 under conditions promoting expression and recovering the G-CSFR.

6. An isolated DNA sequence according to claim 2, comprising nucleotide sequences encoding the sequences of amino acids selected from the group consisting of:
   (a) amino acids 1 through 603 of FIGS. 2A–C; and
   (b) amino acids −3 through 603 of FIGS. 2A–C.

7. A recombinant expression vector comprising a DNA sequence according to claim 6.

8. A host cell transformed or transfected with a recombinant expression vector according to claim 7.

9. A process of preparing a human G-CSF receptor or an analog thereof, comprising culturing a host cell according to claim 8 under conditions promoting expression and recovering the G-CSFR.

10. An isolated DNA sequence according to claim 1, comprising nucleotide sequences encoding the sequences of amino acids selected from the group consisting of:
    (a) amino acids 1 through 759 of FIGS. 2A–C; and
    (b) amino acids −3 through 759 of FIGS. 2A–C.

11. A recombinant expression vector comprising a DNA sequence according to claim 10.

12. A host cell transformed or transfected with a recombinant expression vector according to claim 11.

13. A process for preparing a human G-CSF receptor or an analog thereof, comprising culturing a host cell according to claim 12 under conditions promoting expression and recovering the G-CSFR.

14. A recombinant expression vector comprising a DNA sequence according to claim 1.

15. A host cell transformed or transfected with a recombinant expression vector according to claim 14.

16. A process for preparing a human G-CSF receptor or an analog thereof, comprising culturing a host cell according to claim 15 under conditions promoting expression and recovering the G-CSFR.

* * * * *

UNITED STATES PATENT AND TRADEMARK OFFICE
CERTIFICATE OF CORRECTION

PATENT NO. : 5,422,248  Page 1 of 2
DATED : June 6, 1995
INVENTOR(S) : Craig A. Smith; Alf D. Larsen; John E. Sims, Benson M. Curtis It is certified that error appears in the above-indentified patent and that said Letters Patent is hereby corrected as shown below:

Column 2, line 17, replace "GoCSFR" with -- G-CSFR --.

Column 3, line 16, replace "4:4683" with -- 14:4683 --.

Column 5, line 42, replace "eDNA" with -- cDNA --.

Column 6, line 25, replace "eDNA" with -- cDNA --.
Column 6, line 61, replace "(5x1-10M)" with -- (5x10$^{-10}$M) --.
Colum 7, line 19, please italicize the words in vitro.
Column 7, line 62, replace "co-factor" with -- α-factor --.
Column 8, line 18, replace "hisoxirane" with -- bisoxirane --.
Column 9 line 24, please italicize the words per se.
Column, line 59, replace "eDNA" with -- cDNA --.
Column 9, line 66, replace "fibosomal" with -- ribosomal --.
Column 10, line 11, replace "fibosome" with -- ribosome --.
Column 10, line 21, replace "routants" with -- mutants --.
Column 10, line 68, please italicize the word Pseudomonas.
Column 11, line 1, please italicize the words Streptomyces and Staphylococcus.
Column 11, line 28, replace "cI8571ts" with -- cI857ts --.
Column 11, lines 35 and 36, please italicize the words Saccharomyces, Pichia and Kluyveromyces.
Column 12, line 6, replace "el-factor" with -- α-factor --.
Column 12, line 63, replace "Hind IH" with -- Hind III --.
Column 12, line 64, replace "BglI" with -- BglII --, and italicize Bgl.
Column 16, line 7, replace "convened" with -- converted --.
Column 16, lines 10 and 12, replace "eDNA" with -- cDNA --.
Column 16, line 13, replace "BglII" with -- BglII --, and italicize Bgl.
Column 16, line 14, replace "eDNA" with -- cDNA --.
Column 16, line 19, replace "BglI" with -- BglII --, and italicize Bgl.
Column 16, line 22, replace "eDNA" with -- cDNA --.
Column 16, line 29, replace "eDNA" with -- cDNA --.
Column 16, line 47, replace "Bgl/I" with -- BglI --.
Column 16, line 55, replace "eDNA" with -- cDNA --.

UNITED STATES PATENT AND TRADEMARK OFFICE
CERTIFICATE OF CORRECTION

PATENT NO. : 5,422,248
DATED : June 6, 1995
INVENTOR(S) : Craig A. Smith, et al

It is certified that error appears in the above-indentified patent and that said Letters Patent is hereby corrected as shown below:

Column 16, line 56, replace "DHSA" with -- DH5α --.

Signed and Sealed this

Eighth Day of October, 1996

BRUCE LEHMAN

Attest:

Attesting Officer

Commissioner of Patents and Trademarks